US00PP08919P

United States Patent [19]

Saville

[11] Patent Number: Plant 8,919

[45] Date of Patent: Oct. 4, 1994

[54] MINIATURE ROSE PLANT NAMED SAVAVEL

[75] Inventor: F. Harmon Saville, Rowley, Mass.

[73] Assignee: Nor'East Miniature Roses, Inc., Rowley, Mass.

[21] Appl. No.: 148,206

[22] Filed: Nov. 4, 1993

[51] Int. Cl.[5] ..... A01H 5/00

[52] U.S. Cl. ..... Plt./10

[58] Field of Search ..... Plt. 10

*Primary Examiner*—Howard J. Locker

*Attorney, Agent, or Firm*—Christie, Parker & Hale

[57] ABSTRACT

A new miniature rose with red flowers of good form.

1 Drawing Sheet

SUMMARY OF THE INVENTION

The present innvetion relates to a new and distinct variety of rose plant of the miniature rose class, which was created by me by crossing as seed parent the variety known as 'Rainbow's End' (U.S. Plant Pat. No. 5,482) and as pollen parent the variety known as 'Acey Deucy'(U.S. Plant Pat. No. 5,092). The varietal denomination of this new rose is 'Savavel'.

Among the novel characteristics possessed by this new variety which distinguishes it from its parents and all other varieties of which I am aware is its attractive red flowers of good exhibition form.

Asexual reproduction by propagation of cuttings of the new variety as performed in Essex County, Mass. shows that the foregoing and other distinguishing characteristics come true to form and are established and transmitted through succeeding propagations.

BRIEF DESCRIPTION OF ILLUSTRATION

The accompanying illustration shows typical specimens of the flowers of the new variety in different stages of development depicted in color as nearly true as it is reasonably possible to make the same in a color illustration of this character. Phenotypic expression may vary with light availability, environmental and cultural conditions.

DETAILED DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart.

Parentage:

*Seed parent.*—'Rainbow's End' U.S. Plant Pat. No. 5,482).

*Pollen parent.*—'Acey Deucy' U.S. Plant Pat. No. 5,092).

The following observations are made of specimens grown under glass in Essex County, Mass. during the month of August.

FLOWER

Blooming habit: Continuous.

A. Bud:

(1) *Size.*—Medium.

(2) *Form.*—Pointed.

(3) *Color.*—As sepals divide, bud color is near 46A to C.

(4) *Sepals.*—Slightly longer than bud, slight foliation.

(5) *Peduncle.*—Length — About ¾ inch. Aspect — Straight. Strength — Erect. Color — Near 146C.

B. Bloom:

(1) *Size.*—Average size when fully expanded — About 1¼ inches.

(2) *Borne.*—Singly and several together in large sprays.

(3) *Form.*—High centered at first becoming flat, petals remaining loosely rolled outward.

(4) *Petalage.*—Number of petals under normal conditions — about 27-32.

(5) *Color.*—During first two days, inner petals at center of flower near 45A; outer petals near 45A; base of petals at point of attachment near 12B; reverse of petals near 46A and general tonality from a distance clear red. As bloom ages the color changes to near 46C and the general tonality gets lighter.

C. Petals:

(1) *Texture.*—Thick, firm.

(2) *Appearance.*—Inside velvety and outside satiny.

(3) *Form.*-Ovate, slight point at apex.

(4) *Arrangement.*—Imbricated, regularly arranged, shingle-like.

(5) *Petaloids in center.*—Few.

(6) *Persistence.*—Drop off cleanly.

(7) Fragrance.—None.

(8) *Lasting quality.*—Average.

REPRODUCTIVE ORGANS

A. Stamens, filaments and anthers:

*Arrangement.*—Regularly arranged around styles.

*Color.*—Near 22B.

B. Pollen:

*Color.*—Near 22B.

C. Styles: Medium length, thin, even.

D. Stigmas:

*Color.*—Near 53B.

E. Hips:

*Shape.*—Globular.

*Size.*—About ⅝ inch.

*Color.*—Orange at maturity.

*Seede.*—Seeds do not protrude.

PLANT

A. Form: Compact.

B. Growth: Very vigorous.

*Height attained.*—About 12 to 14 inches.

C. Foliage: Compound 5 to 7 leaflets.

(1) *Size.*—Medium.

(2) *Quantity.*—Abundant.

(3) *Color.*—New Foliage: Upper side — Near 137B. Underside — Near 137B. Old foliage: Upper side — Near 139A. Underside — Near 137B.

(4) *Shape.*—Oval, pointed.

(5) *Texture.*—Upper side is semi-glossy; underside is matte.

(6) *Edge.*—Serrated.

(7) *Serration.*—Regular, shallow.

(8) *Leaf stem.*—Color — Near 183D. Underside — 144B.

(9) *Stipules.*—Small, smooth.

(10) *Resistance to disease.*—Blackspot — Average. Mildew — Average. Rust — Average.

D. Wood:

(1) *New wood.*—Color — Near 146C. Bark — Smooth.

(2) *Old wood.*—Color — Near 138A. Bark — Smooth.

E. Thorns:

*Quantity (main stalk).*—Ordinary.

*On laterals from stalk.*—ordinary.

*Form.*—Flat base, short, very slight curve.

*Length.*—Short.

*Color.*—Near 184C.

*Position.*—Irregular.

*Prickles.*—None.

F. Winter hardiness: Needs protection in severe climates.

I claim:

1. A new and distinct variety of rose plant of the miniature rose class, substantially as shown and described.

* * * * *

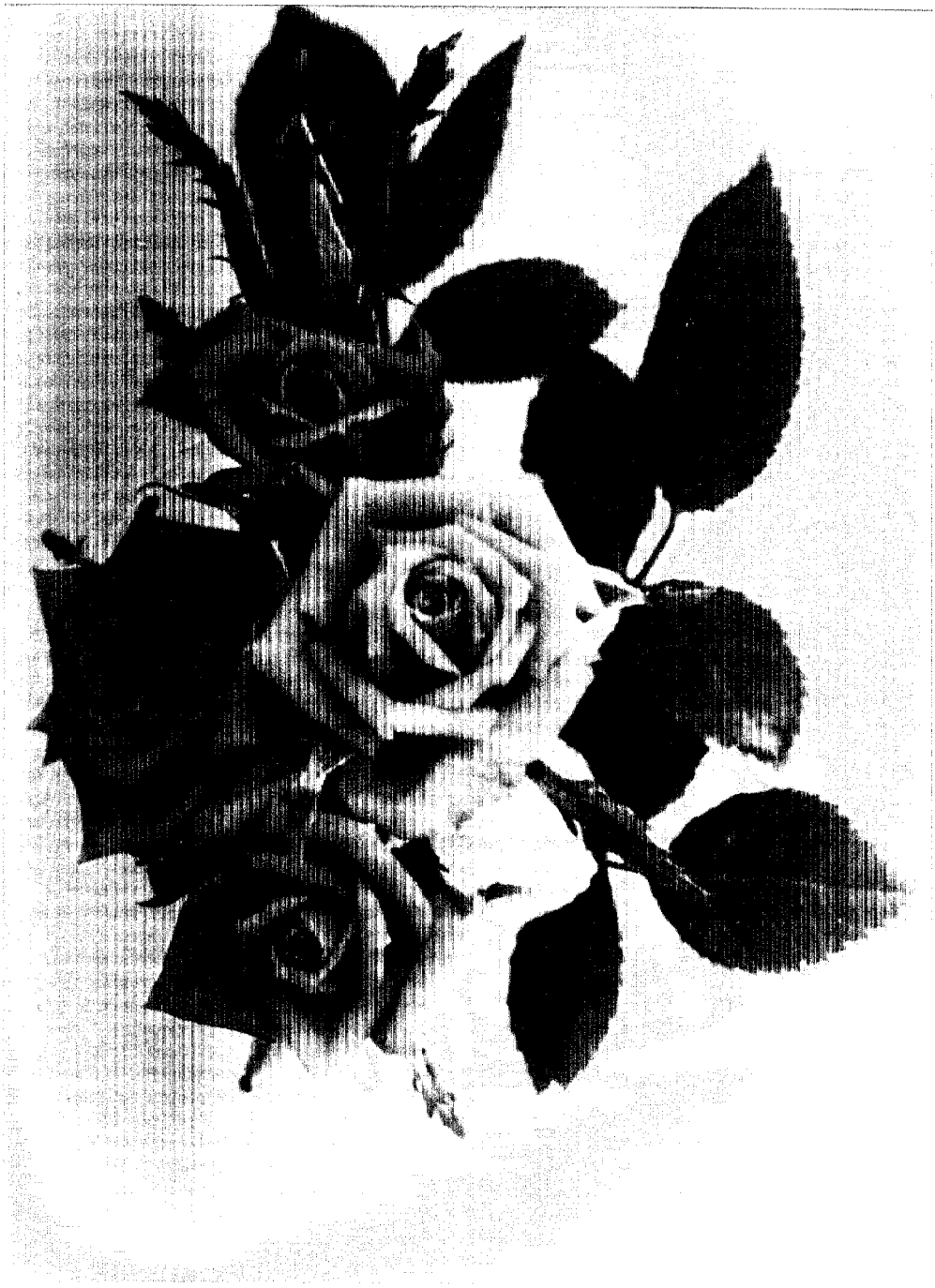

UNITED STATES PATENT AND TRADEMARK OFFICE

CERTIFICATE OF CORRECTION

PATENT NO. : Plant 8,919

DATED : October 4, 1994

INVENTOR(S) : F. Harmon Saville

It is certified that error appears in the above-indentified patent and that said Letters Patent is hereby corrected as shown below:

On the title page;

item [56] References Cited, U.S. References, PATENT DOCUMENTS, after "[58]" insert the following references:

-- [56] References Cited
U.S. PATENT DOCUMENTS

| | | |
|---|---|---|
| P.P. 5,092 | 8/1983 | Saville...Plt.10 |
| P.P. 5,450 | 4/1985 | Saville...Plt.10 |
| P.P. 5,692 | 3/1986 | Saville...Plt.10 |
| P.P. 5,749 | 6/1986 | Saville...Plt.10 -- |

Column 1, line 3, change "innvetion" to -- invention --.

Column 1, lines 43,44, after "5,092)." insert on the next line -- Class: Miniature --.

Column 2, line 50, change "Seede" to -- Seeds --.

Signed and Sealed this

Twenty-first Day of March, 1995

*Attest:*

Bruce Lehman

BRUCE LEHMAN

*Attesting Officer*

*Commissioner of Patents and Trademarks*